(12) United States Patent
Cherkezyan et al.

(10) Patent No.: US 12,198,234 B2
(45) Date of Patent: Jan. 14, 2025

(54) SYSTEMS AND METHODS FOR MOTION DETECTION IN MEDICAL IMAGES

(71) Applicant: GE Precision Healthcare LLC, Milwaukee, WI (US)

(72) Inventors: Lusik Cherkezyan, Libertyville, IL (US); Brian E. Nett, Wauwatosa, WI (US); Jed Douglas Pack, Glenville, NY (US); Jiang Hsieh, Brookfield, WI (US)

(73) Assignee: GE PRECISION HEALTHCARE LLC, Milwaukee, WI (US)

( * ) Notice: Subject to any disclaimer, the term of this patent is extended or adjusted under 35 U.S.C. 154(b) by 450 days.

(21) Appl. No.: 17/454,594

(22) Filed: Nov. 11, 2021

(65) Prior Publication Data

US 2023/0145920 A1 May 11, 2023

(51) Int. Cl.
| | |
|---|---|
| *G06T 5/20* | (2006.01) |
| *A61B 6/00* | (2006.01) |
| *A61B 6/03* | (2006.01) |
| *G06T 5/92* | (2024.01) |
| *G06T 7/00* | (2017.01) |
| *G06T 11/00* | (2006.01) |

(52) U.S. Cl.
CPC ............ *G06T 11/006* (2013.01); *A61B 6/032* (2013.01); *A61B 6/5264* (2013.01); *G06T 5/20* (2013.01); *G06T 5/92* (2024.01); *G06T 7/0012* (2013.01); *G06T 2207/10116* (2013.01); *G06T 2211/416* (2013.01)

(58) Field of Classification Search
CPC . G06T 11/006; G06T 5/20; G06T 5/92; G06T 7/0012; G06T 2207/10116; G06T 2211/416; G06T 2211/412; G06T 11/008; A61B 6/032; A61B 6/5264
See application file for complete search history.

(56) References Cited

U.S. PATENT DOCUMENTS

| | | | |
|---|---|---|---|
| 8,995,735 B2 | 3/2015 | Cao et al. | |
| 2007/0238957 A1* | 10/2007 | Yared | A61B 6/4417 600/407 |

(Continued)

OTHER PUBLICATIONS

Parker, D., "Optimal short scan convolution reconstruction for fan beam CT," Medical Physics, vol. 9, No. 2, Mar. 1982, 5 pages.

(Continued)

*Primary Examiner* — Chan S Park
*Assistant Examiner* — D J Dhooge
(74) *Attorney, Agent, or Firm* — McCoy Russell LLP (57) ABSTRACT

Methods and systems are provided for identifying motion in medical images. In one example, a method includes obtaining projection data of an imaging subject, reconstructing a first image of a location of the imaging subject from the projection data using a first reconstruction technique and reconstructing a second image corresponding to the same location of the imaging subject from the of projection data using a second reconstruction technique, different than the first reconstruction technique in terms of temporal sensitivity, calculating an inconsistency metric quantifying temporal inconsistencies between the first image and the second image, and taking an action based on the inconsistency metric.

19 Claims, 7 Drawing Sheets

(56) References Cited

U.S. PATENT DOCUMENTS

| | | | | |
|---|---|---|---|---|
| 2013/0303884 | A1* | 11/2013 | Kuntz | A61B 5/055 |
| | | | | 600/417 |
| 2016/0367212 | A1* | 12/2016 | Tang | A61B 6/5205 |
| 2017/0004636 | A1* | 1/2017 | Nett | A61B 6/5205 |
| 2017/0079530 | A1* | 3/2017 | DiMaio | A61B 5/0261 |
| 2021/0212656 | A1* | 7/2021 | Fan | A61B 6/482 |

OTHER PUBLICATIONS

Feldkamp, L. et al., "Practical cone-beam algorithm," Journal of the Optical Society of America A, vol. 1, No. 6, Jun. 1984, 8 pages.

Lu, W. et al., "Tomographic motion detection and correction directly in sinogram space," Physics in Medicine and Biology, vol. 47, No. 8, Apr. 21, 2002, 19 pages.

Zou, Y. et al., "Exact image reconstruction on PI-lines from minimum data in helical cone-beam CT," Physics in Medicine and Biology, vol. 49, No. 6, Mar. 21, 2004, 20 pages.

Zhuang, T. et al., "Fan-beam and cone-beam image reconstruction via filtering the backprojection image of differentiated projection data," Physics in Medicine and Biology, vol. 49, No. 24, Dec. 21, 2004, 16 pages.

Pack, J. et al., "Cone-Beam Reconstruction Using the Backprojection of Locally Filtered Projections," IEEE Transactions on Medical Imaging, vol. 24, No. 1, Jan. 2005, 16 pages.

Katsevich, A., "Theoretically Exact Filtered Backprojection-Type Inversion Algorithm for Spiral CT," SIAM Journal on Applied Mathematics, vol. 62, No. 6, Jul. 27, 2006, 15 pages.

Zhao, J. et al., "Feldkamp-type reconstruction algorithms for spiral cone-beam CT with variable pitch," Journal of X-Ray Science and Technology, vol. 15, No. 4, Jan. 2007, 21 pages.

Ens, S. et al., "Sinogram-Based Motion Detection in Transmission Computed Tomography," Proceedings of the 4th European Conference of the International Federation for Medical and Biological Engineering, Nov. 23, 2008, Antwerp, Belgium, 4 pages.

Sepehri, S. et al., "Direct Detection of Small Motion From Dynamic Computed Tomography Images," Proceedings of the 21st European Signal Processing Conference (EUSIPCO 2013), Sep. 9, 2013, Marrakech, Morocco, 5 pages.

Biguri, A. et al., "A general method for motion compensation in x-ray computed tomography," Physics in Medicine and Biology, vol. 62, No. 16, Jul. 24, 2017, 19 pages.

Lossau, T. et al., "Motion Artifact Recognition and Quantification in Coronary CT Angiography using Convolutional Neural Networks," Medical Image Analysis, vol. 52, Feb. 2019, Available Online Nov. 15, 2018, 19 pages.

* cited by examiner

SYSTEMS AND METHODS FOR MOTION DETECTION IN MEDICAL IMAGES

TECHNICAL FIELD

Embodiments of the subject matter disclosed herein relate to imaging, and more particularly, to systems and methods for motion detection in computed tomography images.

BACKGROUND

Non-invasive imaging technologies allow images of the internal structures of a patient or object to be obtained without performing an invasive procedure on the patient or object. In particular, technologies such as computed tomography (CT) use various physical principles, such as the differential transmission of x-rays through the target volume, to acquire image data and to construct tomographic images (e.g., three-dimensional (3D) representations of the interior of the human body or of other imaged structures).

In computed tomography (CT), an x-ray source and an x-ray detector are arranged on opposite sides of a gantry encircling a body of the patient lying on a table, and a cross-sectional image (e.g., slice) of a region of interest (ROI) is reconstructed from x-ray data (e.g., projections) acquired from the body as the x-ray source and the x-ray detector rotate around the body. A position of the table of the gantry may be adjusted in a superior/inferior (SI) direction (e.g. a z-direction) along a central axis of the gantry over time to generate a plurality of slices from which one or more images may be generated. The table may be continuously adjusted in real time, where projections are acquired as the x-ray source follows a trajectory of a spiral or a helix around the patient. The images reconstructed from the slices may be combined to create a 3D volumetric image of the ROI.

SUMMARY

Embodiments for quantifying motion in medical images are provided herein. In one example, a method includes obtaining projection data of an imaging subject, reconstructing a first image of a location of the imaging subject from the projection data using a first reconstruction technique and reconstructing a second image corresponding to the same location of the imaging subject from the projection data using a second reconstruction technique, different than the first reconstruction technique in terms of temporal sensitivity, calculating an inconsistency metric quantifying temporal inconsistencies between the first image and the second image, and taking an action based on the inconsistency metric.

The above advantages and other advantages, and features of the present description will be readily apparent from the following Detailed Description when taken alone or in connection with the accompanying drawings. It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

Various aspects of this disclosure may be better understood upon reading the following detailed description and upon reference to the drawings in which.

DETAILED DESCRIPTION

This description and embodiments of the subject matter disclosed herein relate to methods and systems for quantifying, alerting an operator to, and/or correcting visual artifacts which appear as a result of temporal inconsistencies (e.g. patient motion or breathing). The visual artifacts produced have the potential to ultimately cause the patient to receive improper radiation treatment, excessive radiation delivery, or inaccurate diagnosis. By applying the methods described herein, such visual artifacts can be quantified and corrected for. The disclosed method is highly sensitive to temporal data inconsistencies that are too subtle for temporally-resolved sinogram- or voxel-tracking methods to detect.

In computed tomography, detector data consistency in the temporal domain is paramount for the quality of reconstructed images. Phenomena such as patient motion, table speed variation, data drift, etc., may introduce image artifacts such seen as streaks or blurring. Depending on the severity of the inconsistency, the resultant image artifact can lead to clinically significant implications such as additional patient radiation, inaccurate diagnosis, and/or improper dose and delivery of radiation during therapy. According to embodiments disclosed herein, the severity of undesired clinical consequences may be reduced or eliminated with an approach for identifying motion that is specific to wide cone helical acquisitions and is designed to quantify data inconsistencies in a temporally-resolved manner. Since involuntary patient motion remains one major challenge in tomographic image reconstructions, the detection of any temporal data inconsistencies and "motion detection" may be used interchangeably throughout this disclosure.

The helical scan is the most popular scan mode in clinical computed tomography (CT) diagnostic imaging due to its fast volumetric coverage capability. Exact reconstruction algorithms being too computationally complex, approximate reconstruction algorithms are typically utilized. The analysis framework introduced herein takes advantage of the fact that different approximate solutions lead to different degrees of temporal artifact severity and temporal artifacts can therefore be detected and quantified when two images, generated with more and less inconsistency-sensitive reconstructions, are compared.

Thus, the approach described herein involves the comparison of two images each reconstructed from identical detector data (e.g. a single sinogram) and with different reconstruction techniques (e.g., filtered backprojections with different view weightings). The two reconstruction techniques are chosen in a way that differences between the reconstructed images highlight temporal inconsistencies. In some embodiments, the reconstruction techniques are chosen to have notable differences in noise profiles, helical wide-cone beam artifacts, and magnitudes of motion-induced artifacts. The desired differences in the image reconstructions can, in some cases, be achieved by adjusting the relative weights used in the reconstructions. By evaluating the difference of the two images using one of two types of inconsistency metrics (either in the image domain or the spatial frequency domain), motion can be detected and appropriate action can be taken by the imaging operator to redo the scan or correct for the artifacts.

Figure 1:
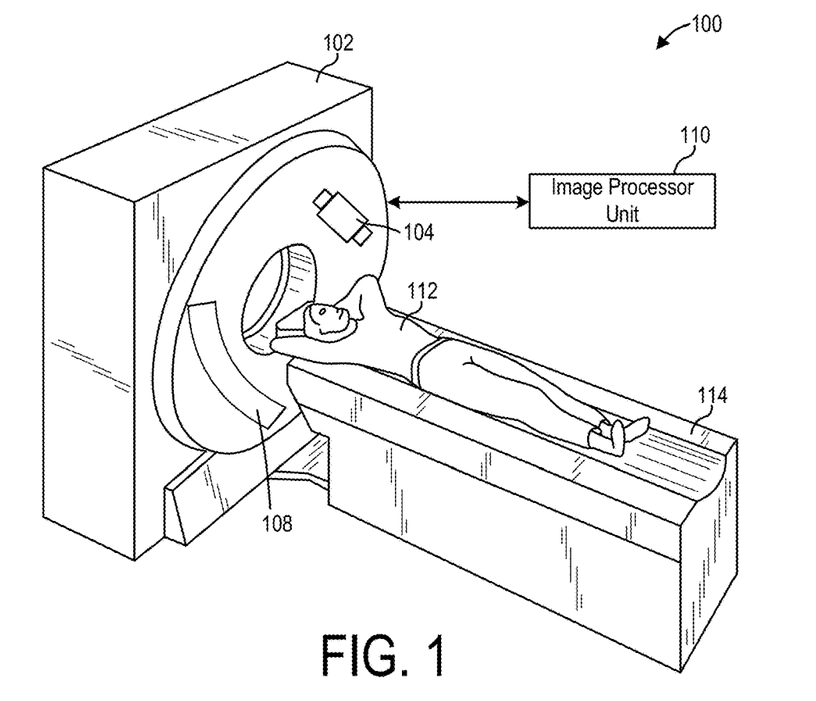
FIG. 1 shows a pictorial view of an imaging system, according to an embodiment.
Figure 2:
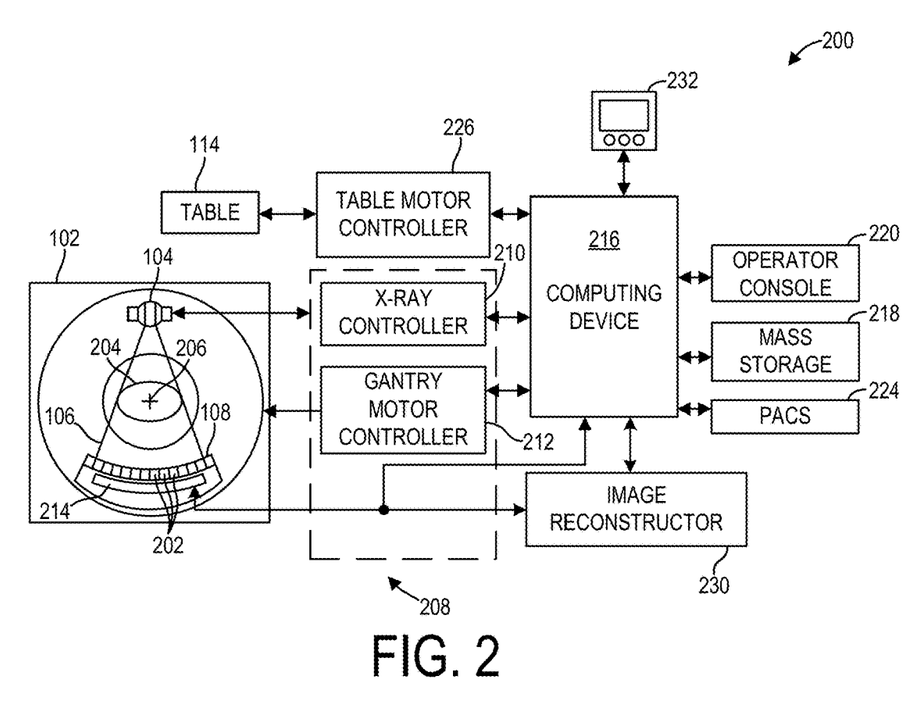
FIG. 2 shows a block schematic diagram of an exemplary imaging system, according to an embodiment.
Figure 3:
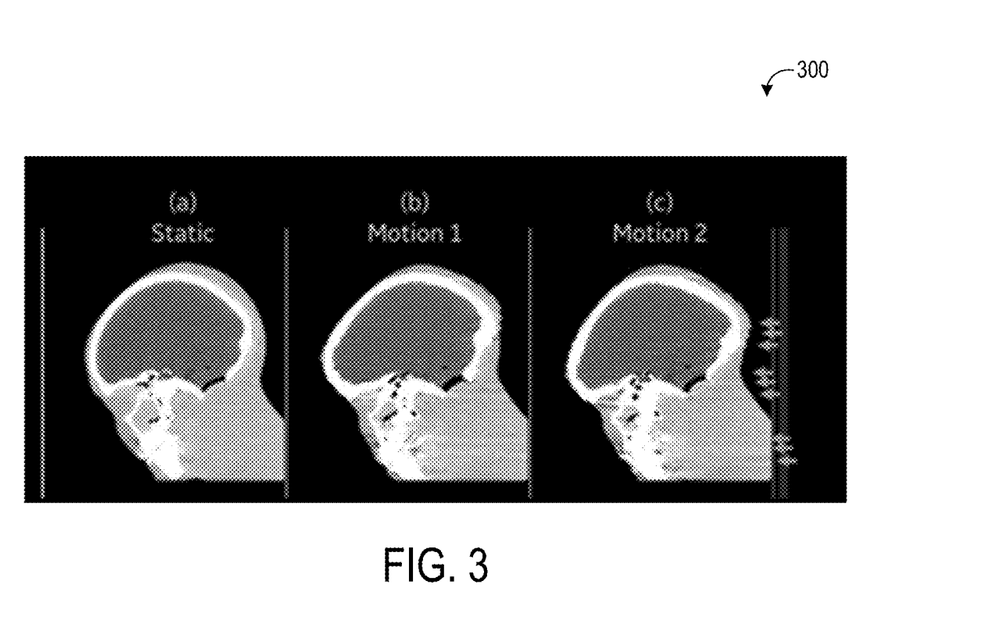
FIG. 3 shows three reconstructed CT images, exemplifying the effects of motion on CT scans.
Figure 8:
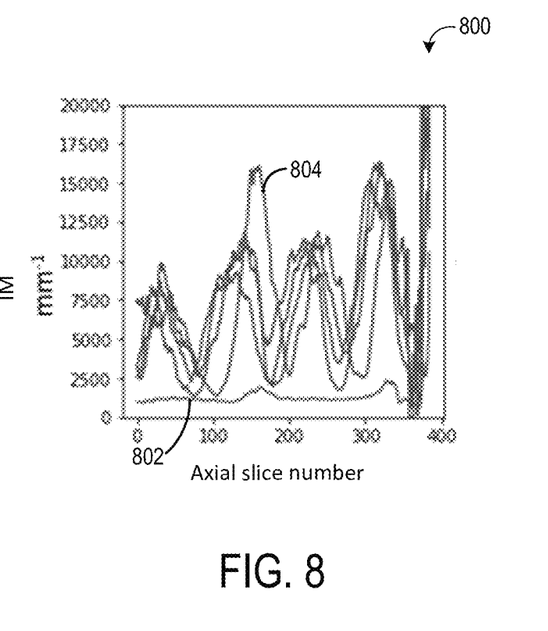
FIG. 8 shows plots of the spatial frequency inconsistency metric computed for each slice (image) of static and moving head phantoms.
Figure 9:
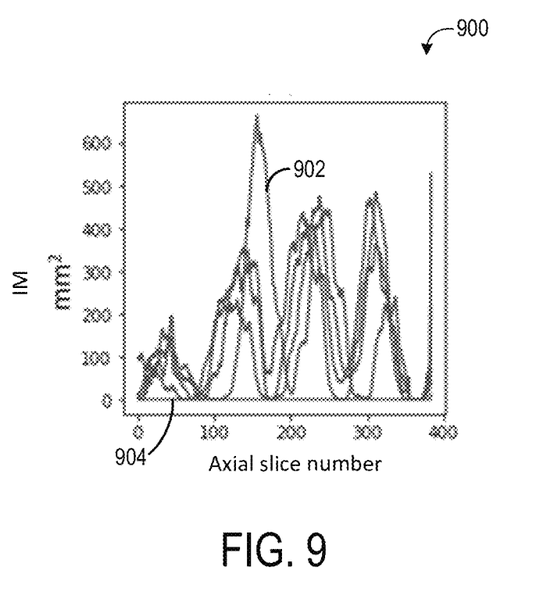
FIG. 9 shows plots of the image domain inconsistency metric computed for each slice (image) of static and moving head phantoms.

An example of a computed tomography (CT) imaging system that may be used to acquire projection data in accordance with the present techniques is provided in FIGS. 1 and 2. Visual reconstruction of the acquired data with a static or moving phantom is shown in FIG. 3, including image artifacts resulting from the moving phantom. This motion can be quantified and corrected for using the method of FIG. 4, which involves generating inconsistency metrics (IMs) based on the methods of FIG. 5 and FIG. 7. FIG. 6 is a visual example of the IM computed using the method of FIG. 5. FIGS. 8 and 9 show the results of the two IMs being applied to all slices of helical CT scans featuring both moving and static head phantoms.

Though a CT system is described by way of example, it should be understood that the present techniques may also be useful when applied to images acquired using other imaging modalities, such as tomosynthesis, PET imaging, C-arm angiography, and so forth. The present discussion of a CT imaging modality is provided merely as an example of one suitable imaging modality.

FIG. 1 illustrates an exemplary CT system 100 configured for CT imaging. Particularly, the CT system 100 is configured to image a subject 112 such as a patient, an inanimate object, one or more manufactured parts, and/or foreign objects such as dental implants, stents, and/or contrast agents present within the body. In one embodiment, the CT system 100 includes a gantry 102, which in turn, may further include at least one x-ray source 104 configured to project a beam of x-ray radiation 106 (see FIG. 2) for use in imaging the subject 112 laying on a table 114. Specifically, the x-ray source 104 is configured to project the x-ray radiation beams 106 towards a detector array 108 positioned on the opposite side of the gantry 102. Although FIG. 1 depicts a single x-ray source 104, in certain embodiments, multiple x-ray sources and detectors may be employed to project a plurality of x-ray radiation beams for acquiring projection data at different energy levels corresponding to the patient. In some embodiments, the x-ray source 104 may enable dual-energy gemstone spectral imaging (GSI) by rapid peak kilovoltage (kVp) switching. In some embodiments, the x-ray detector employed is a photon-counting detector which is capable of differentiating x-ray photons of different energies. In other embodiments, two sets of x-ray sources and detectors are used to generate dual-energy projections, with one set at low-kVp and the other at high-kVp. It should thus be appreciated that the methods described herein may be implemented with single energy acquisition techniques as well as dual energy acquisition techniques.

In certain embodiments, the CT system 100 further includes an image processor unit 110 configured to reconstruct images of a target volume of the subject 112 using an iterative or analytic image reconstruction method. For example, the image processor unit 110 may use an analytic image reconstruction approach such as filtered back projection (FBP) to reconstruct images of a target volume of the patient. As another example, the image processor unit 110 may use an iterative image reconstruction approach such as advanced statistical iterative reconstruction (ASIR), conjugate gradient (CG), maximum likelihood expectation maximization (MLEM), model-based iterative reconstruction (MBIR), and so on to reconstruct images of a target volume of the subject 112. As described further herein, in some examples the image processor unit 110 may use both an analytic image reconstruction approach such as FBP in addition to an iterative image reconstruction approach.

In some CT imaging system configurations, an x-ray source projects a cone-shaped x-ray radiation beam which is collimated to lie within an X-Y-Z plane of a Cartesian coordinate system and generally referred to as an "imaging plane." The x-ray radiation beam passes through an object being imaged, such as the patient or subject. The x-ray radiation beam, after being attenuated by the object, impinges upon an array of detector elements. The intensity of the attenuated x-ray radiation beam received at the detector array is dependent upon the attenuation of an x-ray radiation beam by the object. Each detector element of the array produces a separate electrical signal that is a measurement of the x-ray beam attenuation at the detector location. The attenuation measurements from all the detector elements are acquired separately to produce a transmission profile.

In some CT systems, the x-ray source and the detector array are rotated with a gantry within the imaging plane and around the object to be imaged such that an angle at which the x-ray beam intersects the object constantly changes. A group of x-ray radiation attenuation measurements, e.g., projection data, from the detector array at one gantry angle is referred to as a "view." A "scan" of the object includes a set of views made at different gantry angles, or view angles, during one revolution of the x-ray source and detector. It is contemplated that the benefits of the methods described herein accrue to medical imaging modalities other than CT, so as used herein the term "view" is not limited to the use as described above with respect to projection data from one gantry angle. The term "view" is used to mean one data acquisition whenever there are multiple data acquisitions from different angles, whether from a CT, positron emission tomography (PET), or single-photon emission CT (SPECT) acquisition, and/or any other modality including modalities yet to be developed as well as combinations thereof in fused embodiments.

The projection data is processed to reconstruct an image that corresponds to a two-dimensional slice taken through the object or, in some examples where the projection data includes multiple views or scans, a three-dimensional image of the object. One method for reconstructing an image from a set of projection data is referred to in the art as the filtered back projection (FBP) technique. Transmission and emission tomography reconstruction techniques also include statistical iterative methods such as maximum likelihood expectation maximization (MLEM) and ordered-subsets expectation-reconstruction techniques as well as iterative reconstruction techniques. This process converts the attenuation measurements from a scan into integers called "CT numbers" or "Hounsfield units," which are used to control the brightness of a corresponding pixel on a display device.

To reduce the total scan time, a helical scan may be performed. To perform a helical scan, the table supporting the patient is moved relative to the gantry while the data for the prescribed number of slices is acquired. Such a system generates a single helix from a cone beam helical scan. The helix mapped out by the cone beam yields projection data from which images in each prescribed slice may be reconstructed.

As used herein, the phrase "reconstructing an image" is not intended to exclude embodiments in which data representing an image is generated but a viewable image is not. Therefore, as used herein, the term "image" broadly refers to both viewable images and data representing a viewable image. However, many embodiments generate (or are configured to generate) at least one viewable image.

FIG. 2 illustrates an exemplary imaging system 200 similar to the CT system 100 of FIG. 1. In accordance with aspects of the present disclosure, the imaging system 200 is configured for imaging a subject 204 (e.g., the subject 112 of FIG. 1). In one embodiment, the imaging system 200 includes the detector array 108 (see FIG. 1). The detector array 108 further includes a plurality of detector elements 202 that together sense the x-ray radiation beam 106 (see FIG. 2) that pass through the subject 204 (such as a patient) to acquire corresponding projection data. Accordingly, in one embodiment, the detector array 108 is fabricated in a multi-slice configuration including the plurality of rows of cells or detector elements 202. In such a configuration (e.g., multi-row detector CT or MDCT), one or more additional rows of the detector elements 202 are arranged in a parallel configuration for acquiring the projection data. The configuration may include 4, 8, 16, 32, 64, 128, or 256 detector rows. For example, a 64-slice MDCT scanner may have 64 detector rows with a collimator width of 4 cm, while a 256-slice MDCT scanner may have 256 detector rows with a collimator width of 16 cm. Thus, four rotations of a helical scan performed with the 64-slice MDCT scanner may achieve a detector coverage equivalent to a single rotation of scan performed with the 256-slice MDCT scanner.

In certain embodiments, the imaging system 200 is configured to traverse different angular positions around the subject 204 for acquiring desired projection data. Accordingly, the gantry 102 and the components mounted thereon may be configured to rotate about a center of rotation 206 for acquiring the projection data, for example, at different energy levels. Alternatively, in embodiments where a projection angle relative to the subject 204 varies as a function of time, the mounted components may be configured to move along a general curve rather than along a segment of a circle.

As the x-ray source 104 and the detector array 108 rotate, the detector array 108 collects data of the attenuated x-ray beams. The data collected by the detector array 108 undergoes pre-processing and calibration to condition the data to represent the line integrals of the attenuation coefficients of the scanned subject 204. The processed data are commonly called projections.

In some examples, the individual detectors or detector elements 202 of the detector array 108 may include photon-counting detectors which register the interactions of individual photons into one or more energy bins. It should be appreciated that the methods described herein may also be implemented with energy-integrating detectors.

The acquired sets of projection data may be used for basis material decomposition (BMD). During BMD, the measured projections are converted to a set of material-density projections. The material-density projections may be reconstructed to form a pair or a set of material-density map or image of each respective basis material, such as bone, soft tissue, and/or contrast agent maps. The density maps or images may be, in turn, associated to form a 3D volumetric image of the basis material, for example, bone, soft tissue, and/or contrast agent, in the imaged volume.

Once reconstructed, the basis material image produced by the imaging system 200 reveals internal features of the subject 204, expressed in the densities of two basis materials. The density image may be displayed to show these features. In traditional approaches to diagnosis of medical conditions, such as disease states, and more generally of medical events, a radiologist or physician would consider a hard copy or display of the density image to discern characteristic features of interest. Such features might include lesions, sizes and shapes of particular anatomies or organs, and other features that would be discernable in the image based upon the skill and knowledge of the individual practitioner.

In one embodiment, the imaging system 200 includes a control mechanism 208 to control movement of the components such as rotation of the gantry 102 and the operation of the x-ray source 104. In certain embodiments, the control mechanism 208 further includes an x-ray controller 210 configured to provide power and timing signals to the x-ray source 104. Additionally, the control mechanism 208 includes a gantry motor controller 212 configured to control a rotational speed and/or position of the gantry 102 based on imaging requirements.

In certain embodiments, the control mechanism 208 further includes a data acquisition system (DAS) 214 configured to sample analog data received from the detector elements 202 and convert the analog data to digital signals for subsequent processing. The DAS 214 may be further configured to selectively aggregate analog data from a subset of the detector elements 202 into so-called macro-detectors, as described further herein. The data sampled and digitized by the DAS 214 is transmitted to a computer or computing device 216. In one example, the computing device 216 stores the data in a storage device or mass storage 218. The storage device 218, for example, may include a hard disk drive, a floppy disk drive, a compact disk-read/write (CD-R/W) drive, a Digital Versatile Disc (DVD) drive, a flash drive, and/or a solid-state storage drive.

Additionally, the computing device 216 provides commands and parameters to one or more of the DAS 214, the x-ray controller 210, and the gantry motor controller 212 for controlling system operations such as data acquisition and/or processing. In certain embodiments, the computing device 216 controls system operations based on operator input. The computing device 216 receives the operator input, for example, including commands and/or scanning parameters via an operator console 220 operatively coupled to the computing device 216. The operator console 220 may include a keyboard (not shown) or a touchscreen to allow the operator to specify the commands and/or scanning parameters.

Although FIG. 2 illustrates one operator console 220, more than one operator console may be coupled to the imaging system 200, for example, for inputting or outputting system parameters, requesting examinations, plotting data, and/or viewing images. Further, in certain embodiments, the imaging system 200 may be coupled to multiple displays, printers, workstations, and/or similar devices located either locally or remotely, for example, within an institution or hospital, or in an entirely different location via one or more configurable wired and/or wireless networks such as the Internet and/or virtual private networks, wireless telephone networks, wireless local area networks, wired local area networks, wireless wide area networks, wired wide area networks, etc.

In one embodiment, for example, the imaging system 200 either includes, or is coupled to, a picture archiving and communications system (PACS) 224. In an exemplary implementation, the PACS 224 is further coupled to a remote system such as a radiology department information system, hospital information system, and/or to an internal or external network (not shown) to allow operators at different locations to supply commands and parameters and/or gain access to the image data.

The computing device 216 uses the operator-supplied and/or system-defined commands and parameters to operate a table motor controller 226, which in turn, may control a table 114 which may be a motorized table. Specifically, the table motor controller 226 may move the table 114 for appropriately positioning the subject 204 in the gantry 102 for acquiring projection data corresponding to the target volume of the subject 204.

As previously noted, the DAS 214 samples and digitizes the projection data acquired by the detector elements 202. Subsequently, an image reconstructor 230 uses the sampled and digitized x-ray data to perform high-speed reconstruction. Although FIG. 2 illustrates the image reconstructor 230 as a separate entity, in certain embodiments, the image reconstructor 230 may form part of the computing device 216. Alternatively, the image reconstructor 230 may be absent from the imaging system 200 and instead the computing device 216 may perform one or more functions of the image reconstructor 230. Moreover, the image reconstructor 230 may be located locally or remotely, and may be operatively connected to the imaging system 200 using a wired or wireless network. Particularly, one exemplary embodiment may use computing resources in a "cloud" network cluster for the image reconstructor 230.

In one embodiment, the image reconstructor 230 stores the images reconstructed in the storage device 218. Alternatively, the image reconstructor 230 may transmit the reconstructed images to the computing device 216 for generating useful patient information for diagnosis and evaluation. In certain embodiments, the computing device 216 may transmit the reconstructed images and/or the patient information to a display or display device 232 communicatively coupled to the computing device 216 and/or the image reconstructor 230. In some embodiments, the reconstructed images may be transmitted from the computing device 216 or the image reconstructor 230 to the storage device 218 for short-term or long-term storage.

If the patient 112 is moving relative to the intended trajectory of the table during the scan, artifacts may be produced in the reconstructed image, an example of which is shown in FIG. 3. For example, horizontal streaks may be produced in the image, possibly obscuring important bodily features within the scan. In order to alert the operator (and possibly correct for the defects with image processing), the temporal inconsistencies can be detected and corrected via the method shown in FIG. 4 and explained in more detail below. The operator may be notified by a suitable mechanism, including, for example, a message box displayed on the display device 232.

FIG. 3 shows a set of images 300 illustrating the effects of sinusoidal motion on resulting images reconstructed from projection data obtained by a CT imaging system imaging a phantom. The set of images 300 were obtained with a 64-slice detector coverage, normalized pitch values of 1.0 and 0.5, and slice thickness of 0.625 mm. In image (a), a static phantom shows little to no steaking associated with time-domain inconsistencies (e.g., motion). In images (b) and (c), sinusoidal motions in the sagittal plane are introduced to the phantom during two different acquisitions, resulting in streaking artifacts. In image (c), arrows point to the axial locations of the most severe artifacts. In a patient, such artifacts may obscure important information contained in the image, and thus it may be beneficial to quantify the severity of the distortions that may be introduced in the images, and take corrective action to reduce or prevent such distortions. The methods described herein provide such quantification.

Figure 4:
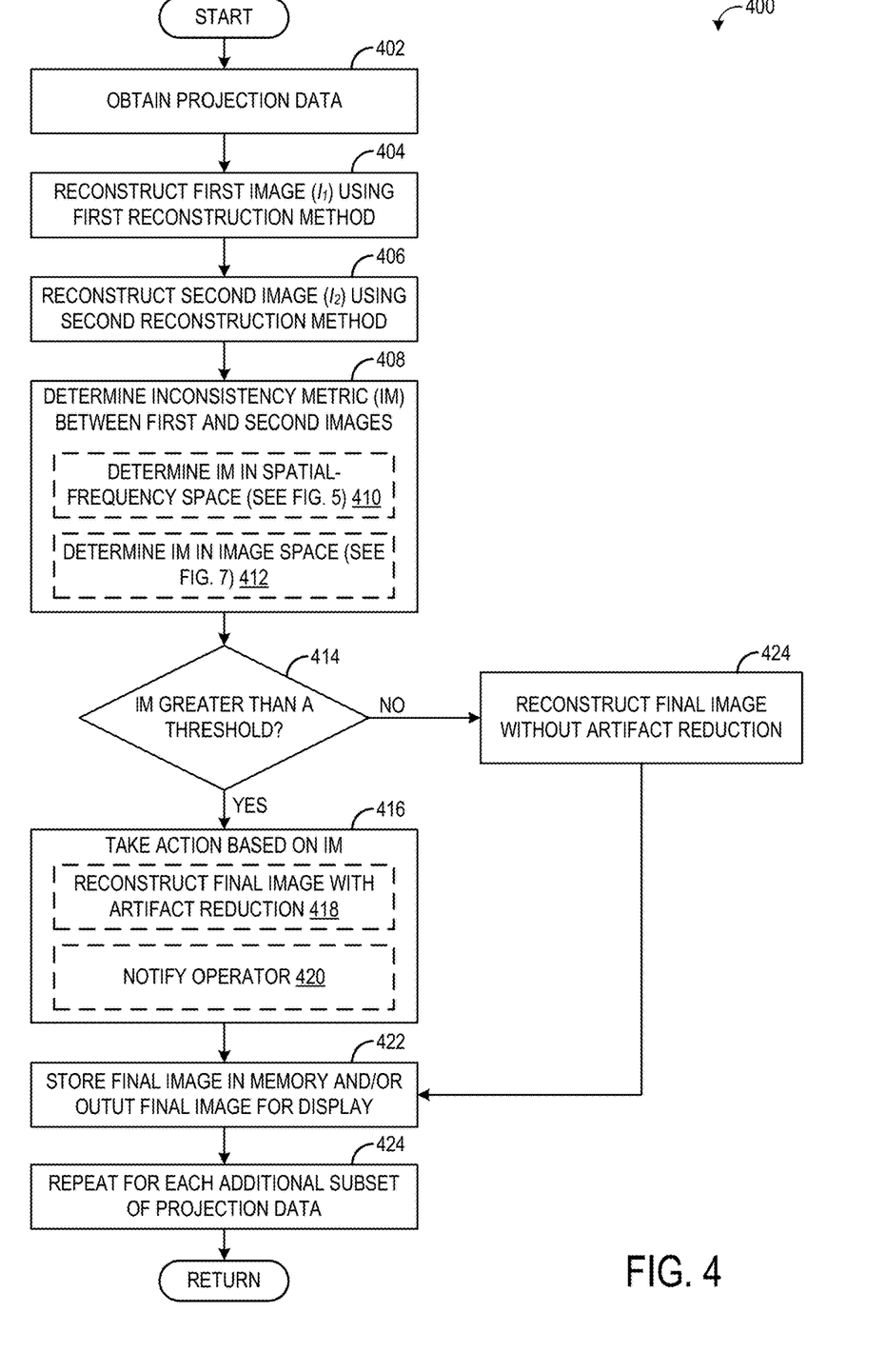
FIG. 4 is a flow chart illustrating a high-level method for detecting motion in reconstructed CT images and taking action based on the motion according to an embodiment of the disclosure.

Referring to FIG. 4, a flowchart of a method 400 is shown for detecting motion of a subject during imaging with a medical imaging system. Method 400 is described with regard to the systems and components of FIG. 1-2, though it should be appreciated that the method 400 may be implemented with other systems and components without departing from the scope of the present disclosure. Method 400 may be carried out according to instructions stored in non-transitory memory of a computing device, such as computing device 216 of FIG. 2.

At 402, projection data is obtained of an imaging subject, such as a patient. The projection data may be obtained with a CT imaging system, such as the system of FIGS. 1 and 2. To obtain the projection data, electrical impulses from the detector array 108 are processed as the x-ray source 104 is activated and gantry 102 spins and the table 114 moves axially simultaneously. The output of the detector array 108 represents reception of x-rays (that are emitted from the x-ray source 104) after the x-rays travel through and around the patient 112, and is in the form of raw tomography data that may be reconstructed to generate images of the patient's body. In some examples, the projection data may be obtained in approximate real time as the method is performed. In other examples, the projection data may be obtained prior to execution of method 400 and may be retrieved from permanent memory.

At 404, a first image ($I_1$) of a location of the imaging subject is reconstructed using a first reconstruction technique. The first image may be reconstructed from a subset of projection data, which may be some or all of the projection data obtained at 402. Additional details of the first reconstruction technique are provided below. At 406, a second image ($I_2$) of the same location (e.g., same as the location of the first image) of the imaging subject is reconstructed using a second reconstruction technique that is different than the first reconstruction technique. The first image and the second image are reconstructed from the same subset of projection data such that the first and second images are of the same slice and thus image the same aspects (e.g., anatomy) of the imaging subject.

Various reconstruction methods may be used in order to reconstruct the first and second image, $I_1$ and $I_2$, at respective steps 404 and 406, according to the disclosure. That is, generally the two reconstructions $I_1$ and $I_2$ can be obtained using any two different reconstruction techniques that differ in the temporal range of projection data used in the reconstruction. For example, the first image may be reconstructed with a first reconstruction technique that includes a first, wider temporal range of projection data (e.g., detector data collected over 180° plus the fan angle of rotation of the gantry) and the second image may be reconstructed with a second reconstruction technique that includes a second, narrower temporal range of projection data (e.g., detector data collected over 180° or less of gantry rotation). Different image reconstructions may, in some embodiments, be the same reconstruction method, such as Feldkamp-Davis-Kress (FDK)-type reconstructions, which differ in their view-weighting functions. In other examples, different image reconstructions may be different reconstruction methods. The two different image reconstructions used to reconstruct the first and second images may, for example, be two FDK-type algorithms with different weightings, an FDK-type reconstruction and Katsevich-type exact reconstruction, an FDK-type reconstruction and a Pi-line type exact inversion, exact analytic method (e.g. Katsevich type or Pi-line type) and iterative reconstruction, or FDK-type reconstruction and iterative reconstruction. More generally, combinations of FDK-type (with different weightings), exact reconstructions (for instance Katsevich type or Pi-line type), and iterative reconstruction may be used to reconstruct first and second image, $I_1$ and $I_2$, at respective steps 404 and 406, so long as the steps are complementary.

As explained above, in some examples, the same reconstruction method may be applied but with different view-weighting functions. View-weighting functions serve to emphasize different locations within reconstruction data. For example, each small region in the object is irradiated by the X-ray beam for some subset of the views. In a helical scan, the size of this subset typically depends on the pitch of the helical acquisition. For example, if a pitch of 0.5 is used during acquisition, a small region of the image volume may project onto the detector for about two full rotations of data. One view weighting function might use (e.g., to backproject) data from all these views with a roughly constant weight. This would result in a broad temporal sensitivity profile for this particular image region. A temporal sensitivity profile indicates how much the image changes when the data acquired at each time is changed by a fixed amount. A second view weighting function might weigh most of the views by 0 and only keep the data corresponding to a minimum window necessary for reconstruction (180 degrees of data). This would result in a narrow temporal sensitivity profile. As an example, an unweighted projection data P(row,col,view), where row and col represent locations in acquired projection data by the detector (e.g., rows and columns of detector pixels), can be weighted by a function w(row, col, view,x,y,z) prior to reconstructing the section of an image corresponding to the location (x,y,z) inside the imaging subject. The weighted projection data is represented by P(row,col,view)*w(row,col,view,x,y,z). Different choices of w(row,col,view,x,y,z) constitute different weightings of the projection data. For example, when an FDK-type reconstruction method is applied, a first weighting function may be applied for the first image, where the first weighting function reduces the weights of unmeasured projections, and a second weighting function may be applied for the second image, where the second weighting function constrains the reconstruction to a minimum projection/data range.

The different reconstruction methods or view weighting functions used to reconstruct the first and second images are such that the resultant images have differences the magnitude of motion-related artifact. Thus, as described below, the motion-related artifact may be identified and quantified based on the first and second images, either in the spatial frequency domain or the image domain. It is to be appreciated that "view weighting" of a reconstruction technique is one way of expressing the temporal sensitivity and thus "view weighting" and "temporal sensitivity" may be used interchangeably throughout this disclosure.

At 408, an inconsistency metric (IM) is determined between the first and second images. Briefly, the IM quantifies differences between $I_1$ and $I_2$ which occur due to patient motion. In some examples, determining the IM may include determining the IM in spatial frequency space, as indicated at 410. Additional details regarding determining the IM in spatial frequency space are provided below with respect to FIG. 5. In some examples, determining the IM may include determining the IM in image space, as indicated at 412. Additional details regarding determining the IM in image space are provided below with respect to FIG. 7.

At 414, the IM computed at 408 is compared to a pre-determined threshold to determine if the IM is greater than the threshold. In some examples, the pre-determined threshold may be set empirically based on visual inspection of images to determine what level of IM leads to visually significant motion artifacts. Depending on the specifics of the reconstruction technique that is being used, it is possible for some motion to take place but not lead to a visible artifact in an image. In this case, the IM would sense the motion and thus the IM would be greater than zero, but an action would not be demanded due to such small motion, and hence the threshold may be non-zero. Thus, the threshold may be chosen such that no artifact correction algorithms apply when the IM is below the threshold. In some examples, the threshold may be based on the specific imaging protocol, anatomy being imaged, and/or reconstruction technique applied. If the IM is not greater than the threshold, method 400 proceeds to 424 where the final image is reconstructed (e.g., from the subset of projection data) without applying a motion artifact reduction technique. The image reconstruction technique applied at 424 may depend on the type of scan, the diagnostic goal of the scan, and/or other variables. In some examples, the final image may be generated by applying complementary frequency filters to $I_1$ and $I_2$ and blending the filtered frequencies, which may reduce cone beam artifacts. To apply the complementary frequency filters, each of the first and second images may be transformed to the frequency domain and a respective, complementary filter applied to each frequency domain image. The filter applied to the first image may keep low frequency content while filtering high frequency content, while the filter applied to the second image may keep the high frequency content while filtering the low frequency content. The filtered transformed images may then be transformed back to the image domain (e.g., by applying an inverse transform) and the two images blended to form a final image, or the filtered frequency components may be summed and the summed frequency components may be inverse transformed back to the image domain. In other examples, the projection data may be reconstructed using any suitable reconstruction technique, or one of the first image or second image may be selected as the final image.

If instead the IM is greater than the threshold at 414, an action is taken at 416 based on the IM. In some embodiments, the operator is notified at 420. For example, a notification may be output for display on a display device of the CT imaging system indicating patient motion, which may allow the operator to initiate a rescan, if desired. In some examples, the operator may be notified only in response to the IM being greater than a second threshold, higher than the threshold. Smaller amounts of motion may be corrected for, as explained below, while larger amounts of motion may trigger a rescan, and thus the operator may be notified in the instance of higher amounts of motion. In some embodiments, in response to the IM being greater than the threshold, taking an action includes applying motion artifact reduction during final image reconstruction, as indicated at 418. For example, the motion artifacts may be corrected for by tracking anatomical features of the patient across adjacent slices and compensating for their relative motion (e.g., by adjusting pixel values in regions with motion based on those regions in adjacent slices), by tracking projection data across consecutive acquisitions and compensating the acquisitions that took place when motion occurred using the neighboring acquisitions, by adapting the image reconstruction technique such that the projections acquired at time points without patient motion are weighted heavier than the ones acquired when the motion occurred, or by an adjustment to the complementary frequency filters approach described above, where the low frequency content is not blended into the final image. In other examples, the final image may be reconstructed from the projection data (e.g., the subset of projection data) using any suitable reconstruction technique with motion artifact reduction, including identical or different methods from those employed in 404 and 406, with or without additional corrections designed to minimize visual artifacts. In either case, the final image is stored in memory and/or output onto a display at 422.

At 424, the above process is repeated for each additional subset of projection data. For example, the projection data may include an entire volume of projection data and the subset of projection data used to reconstruct the first image, the second image, and the final image may be only a portion of the projection data acquired during the scan of the imaging subject. For each additional subset of projection data, two images may be reconstructed using the two different reconstruction techniques described above and an inconsistency metric may be calculated for each additional subset of projection data based on the respective two images, as explained above. An action may be taken for each inconsistency metric in the manner explained above (e.g., reconstruct with or without motion artifact correction), such that the method disclosed herein may generate one IM for each axial image and only the images with corresponding projections acquired when the temporal inconsistency took place (which may be only one or a few images out of the entire volume of images) may be corrected for motion artifacts and projections/images without artifacts may not be corrected.

Figure 5:
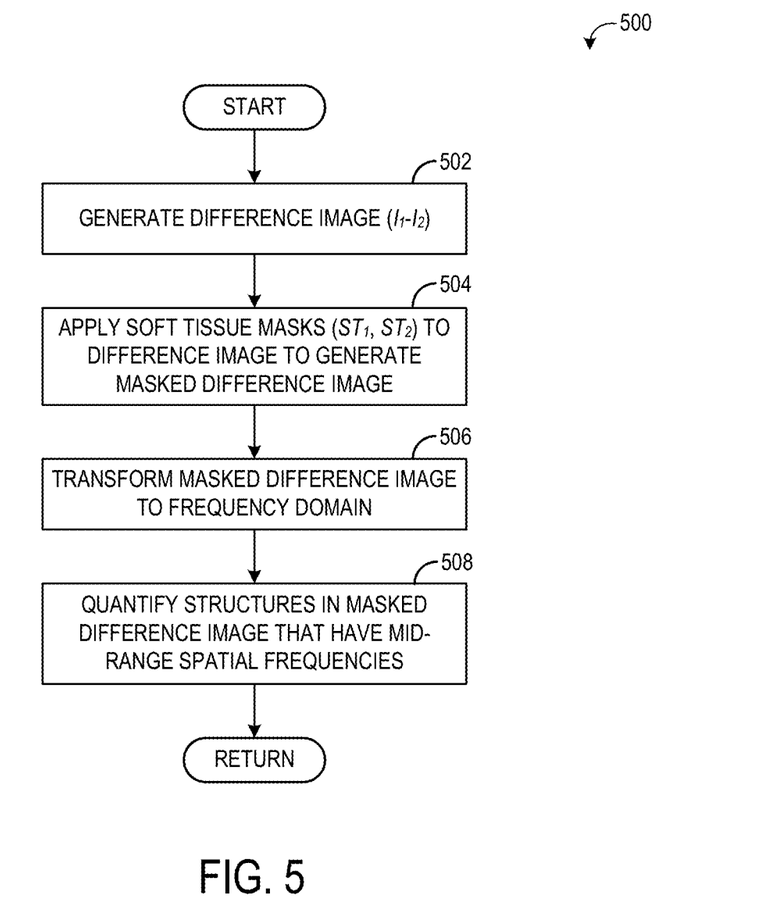
FIG. 5 is a flowchart illustrating a method for quantifying motion with an inconsistency metric calculated in the spatial frequency domain, according to an embodiment of the disclosure.
Figure 6:
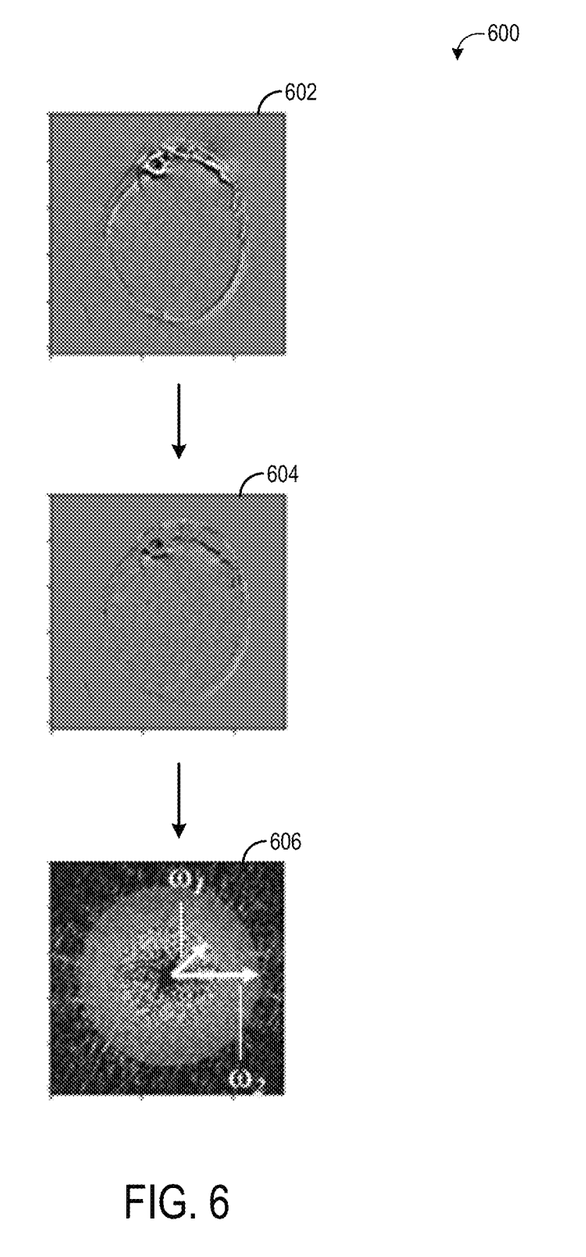
FIG. 6 visually depicts an example process of computing an inconsistency metric in the spatial frequency domain.

FIG. 5 is flow chart illustrating a method 500 for computing the IM in spatial frequency space. Method 500 may be performed as part of method 400, such as at 410 of FIG. 4. At 502, a difference image $I_1-I_2$ is calculated. The difference image is the difference between the first image $I_1$ and the second image $I_2$ generated as described above with respect to FIG. 4. Soft tissue mask matrices $ST_1$ and $ST_2$ are applied to the difference image $I_1-I_2$ at 504 to generate a masked difference image. The soft tissue masks $ST_1$ and $ST_2$ (corresponding to $I_1$ and $I_2$ respectively) are used to minimize the dependence of the IM on the anatomical content of the corresponding axial images. The soft tissue masks $ST_{1,2}$ are matrices with the same dimensions as $I_{1,2}$ and are defined to equal 1 in areas where the CT number (e.g., pixel brightness) in the corresponding image $I_{1,2}$ corresponds to soft tissue (e.g., the CT number is between thresholds of −300 and 125HU), and to equal 0 elsewhere. In some examples, the soft tissue masks may be applied to each image individually before the difference image is calculated.

At 506, the masked difference image generated at 504 is transformed to the spatial frequency domain (e.g., using a Fourier transform, wavelet transform, or Laplace transform). Within the transformed image, regions (e.g., structures in the masked difference image) with mid-range spatial frequencies are identified and quantified at 508.

Here, "mid-range" refers to any frequency between the two pre-determined spatial frequencies $\omega_1$ and $\omega_2$. The quantified mid-range spatial frequency content is returned as the frequency-domain inconsistency metric of 410 of FIG. 4. One example of an overall equation for the IM in the spatial-frequency domain is $$IM = \int_{\omega_1}^{\omega_2} d\omega \frac{\int_0^{2\pi} |FFT\{(I_1-I_2) \times ST_1 \times ST_2\}| d\theta}{2\pi}.$$

Here, the absolute value of the FFT of the masked image difference is integrated around a ring in the frequency domain with a width of $\omega_2-\omega_1$. It is integrated around the entire circumference of the ring: $0 \leq \theta \leq 2\pi$. The distance from the center of the transformed image represents the (real) frequency $\omega$ and the angle $\theta$ with respect to the positive x-axis represents the phase offset of that component.

FIG. 6 shows a process 600 corresponding to method 500, which is applied to calculate the IM for an example subset of projection data. A difference image 602 is generated, which as described above is the difference (e.g., in pixel brightness values) of the first and second images. The soft tissue masks are applied to the difference image to form a masked image 604. A spatial frequency image 606 shows the absolute value (complex modulus) of the FFT of the masked difference image. Two arrows are shown to illustrate $\omega_1$ and $\omega_2$, the limits of integration described in the formula above. The integration region, as described in the equation above, is all points in the ring between the radii $\omega_1$ and $\omega_2$. The factor $$\frac{1}{2\pi}$$

is a normalization constant.

Figure 7:
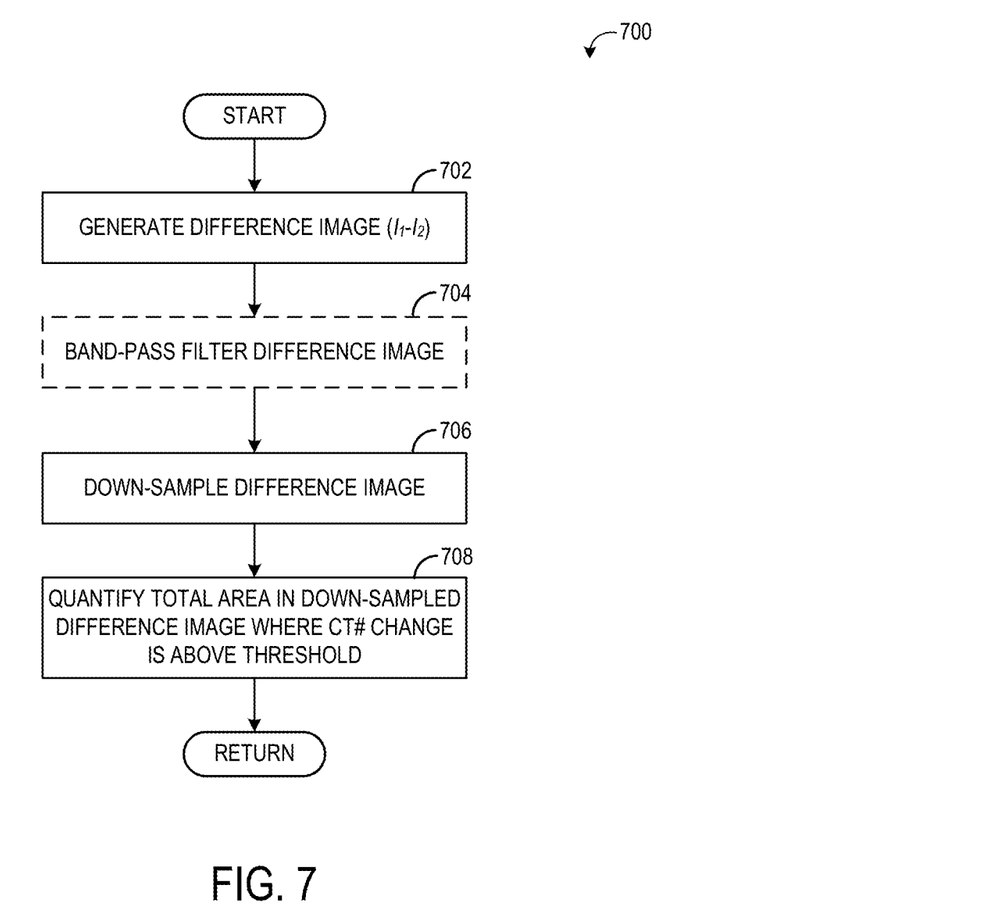
FIG. 7 is a flowchart illustrating a method for quantifying motion with an inconsistency metric calculated in the image domain, according to an embodiment of the disclosure.

FIG. 7 shows a method 700 for generating an IM in the image domain. Method 700 may be performed as part of method 400, such as at 412 of FIG. 4. The advantages of calculating the IM in the image domain relative to the calculation of the IM in the spatial frequency domain may be seen in cases when the patient motion has led to a localized change in the positioning of anatomical structures, such as in cases with patient throat motion during a scan. As a result, the difference between $I_1$ and $I_2$ is large in terms of CT number but, at the same time, is localized to a very small area and can be challenging to quantify for whole-image spatial-frequency quantification. In addition, if the artifact is deemed to be localized to a defined area, this approach allows the possible correction of the artifact to be targeted only to the affected region.

At 702, a difference image is calculated (e.g., generated). The difference image is the difference between the first image $I_1$ and the second image $I_2$ generated as described above with respect to FIG. 4. Optionally, the difference image can be band-pass filtered at 704. The band-pass filter may, in some examples, filter out both high- and low-frequency noise. Filtering of high-frequency noise may improve the accuracy of motion detection by reducing noise.

Filtering of low-frequency noise may reduce visual artifacts produced by uneven x-ray exposure. The image is down-sampled at 706 in the axial plane to reduce noise. Down-sampling is the process of converting an image from a higher resolution to a lower resolution and may be accomplished, in some examples, by nearest-neighbor interpolation, cubic interpolation, or bilinear interpolation. Down-sampling the image may minimize noise-related differences between the first and second images. At 708, the IM is calculated as the total area (e.g. in $mm^2$) in the (possibly band-pass filtered) down-sampled difference image where the absolute value of the CT# is above a pre-determined threshold, which may be determined in a similar manner to the threshold described above with respect to FIG. 5. It should be noted that, in some examples, the thresholds utilized at 508 and 708 may have different numerical magnitudes.

FIG. 8 shows a graph 800 depicting the results of the spatial frequency IM calculation on the moving and static phantoms of FIG. 3. The horizontal axis corresponds to the axial location of the slice (axial slice #) which, due to the nature and the setup of this specific scan, also corresponds to the time of acquisition. Line 802 represents the IM calculated for the static head phantom, where the static head phantom shows a relatively low, constant IM. The sinusoidal nature of the phantom's motion is reflected by the other lines shown in graph 800, such as line 804, that represent the IM calculated with the phantom moving for four separate acquisitions.

FIG. 9 is similar to FIG. 8, showing a graph 900 of the results of the calculation of the image space IM. As is visible, the image space IM may also accurately characterize the sinusoidal motion of the moving head phantom. The IM of the static phantom is shown by line 904 and the IM of the moving phantom in four different acquisitions is shown by the remaining lines in graph 900, such as line 902.

Thus, as explained herein, temporal data inconsistency due to effects such as involuntary patient motion is a universal challenge for the image quality in any tomographic image reconstructions, with various approaches being previously developed to sense its presence or quantify its magnitude. Previously-proposed methods have focused on motion quantification through (a) sinogram-space time-resolved tracking. (b) image-space tracking of anatomical feature positions in time, and (c) deep-learning based recognition of motion artifact presence in the final image.

The approach presented herein analyzes reconstructed images as opposed to sinograms as in methods in group (a). In addition, it does not rely on motion being dramatic enough to lead to structural displacement as in (b). Finally, it is founded on the robust analytical evaluation of motion as opposed to an empirically trained neural network as in (c).

Involuntary patient motion, such as peristaltic, respiratory, or heart motion, results in various artifacts such as blurring and streaks in tomographic images. The inconsistency metric disclosed herein identifies and quantifies any temporal inconsistencies in acquired tomographic data (including those due to patient motion, table speed variations, data drift, etc.) as well as specifies the axial images affected by the temporal inconsistencies. This information can be used to notify the operator of the imaging system or other clinician of the presence and axial location of the artifact(s) to guide targeted rescanning, improve image quality by implementing artifact reduction techniques as appropriate, leading to an improved diagnosis as well as improvement of image post-processing steps such as segmentation, and improve the accuracy of delivery and dose allocation in radiation therapy using the improved images. For example, the IM may be computed in real time, during, for example, a CT scan. Real-time calculation of the IM may be used as a means to gate a radiation source used during radiation therapy. e.g. by turning the radiation therapy source on when the patient is positioned correctly and off while the radiation source is not aimed at the appropriate region. In this way, unnecessary radiation exposure may be reduced.

A technical effect of calculating an inconsistency metric from two images of the same location reconstructed from the same or similar projection data using two reconstruction techniques that differ in temporal sensitivity is that imaging subject motion may be detected in a manner that is highly sensitive to temporal data inconsistencies that cannot be detected with current temporally-resolved sinogram- or voxel-tracking methods, identifies only the inconsistencies/motion that have led to artifacts in the reconstructed images, acts in a time-resolved manner, is anatomy agnostic (e.g., metric values (if desired) can be independent of the underlying anatomy, including the specific organs being imaged or the presence of contrast agents), and is founded on the robust understanding of the underlying physics of image generation and is not empirical.

The disclosure also provides support for a method, comprising: obtaining projection data of an imaging subject, reconstructing a first image of a location of the imaging subject from the projection data using a first reconstruction technique and reconstructing a second image corresponding to the same location of the imaging subject from the projection data using a second reconstruction technique, different than the first reconstruction technique in terms of temporal sensitivity, calculating an inconsistency metric quantifying temporal inconsistencies between the first image and the second image, and taking an action based on the inconsistency metric. In a first example of the method, the first reconstruction technique and the second reconstruction technique comprise different reconstruction methods. In a second example of the method, optionally including the first example, the first reconstruction technique and the second reconstruction technique comprise a same reconstruction method with different view weightings. In a third example of the method, optionally including one or both of the first and second examples, calculating the inconsistency metric comprises generating a difference image representing differences in pixel intensity values between the first image and the second image and calculating the inconsistency metric from the difference image in either a frequency domain or an image domain. In a fourth example of the method, optionally including one or more or each of the first through third examples, calculating the inconsistency metric from the difference image in the frequency domain comprises: applying one or more soft tissue masks to the difference image to generate a masked difference image, transforming the masked difference image to the frequency domain, and quantifying an amount of structures with mid-range spatial frequencies, where the inconsistency metric is the amount of structures with the mid-range spatial frequencies. In a fifth example of the method, optionally including one or more or each of the first through fourth examples, calculating the inconsistency metric from the difference image in the image domain comprises: down-sampling the difference image, and quantifying a total area in the down-sampled difference image where an absolute change in pixel brightness is above a threshold value, where the inconsistency metric is the total area. In a sixth example of the method, optionally including one or more or each of the first through fifth examples, the method further comprises: band-pass filtering the difference image prior to the down-sampling. In a seventh example of the method, optionally including one or more or each of the first through sixth examples, taking an action based on the inconsistency metric comprises determining that the inconsistency metric is greater than a first threshold, and in response, applying a motion artifact correction technique to a final image reconstructed from the projection data and saving the final image and/or displaying the final image. In an eighth example of the method, optionally including one or more or each of the first through seventh examples, taking an action based on the inconsistency metric comprises determining that the inconsistency metric is not greater than a first threshold, and in response, saving a final image reconstructed from the projection data and/or displaying the final image, wherein a motion artifact correction technique is not applied to the final image. In a ninth example of the method, optionally including one or more or each of the first through eighth examples, taking an action based on the inconsistency metric comprises determining that the inconsistency metric is greater than a second threshold, and in response, outputting a notification of patient motion on a display device. In a tenth example of the method, optionally including one or more or each of the first through ninth examples, obtaining the projection data comprises obtaining the projection data via a computed tomography imaging system, wherein the projection data comprises a subset of projection data of an entire volume of projection data of the imaging subject, and further comprising calculating an additional inconsistency metric for each additional subset of projection data of the entire volume of projection data of the imaging subject and taking an action based on each additional inconsistency metric.

The disclosure also provides support for an imaging system, comprising: an x-ray source configured to emit x-rays towards a subject, a detector array comprising a plurality of detector elements configured to detect x-rays attenuated by the subject, a computing device communicatively coupled to the x-ray source and the detector array, the computing device configured with instructions in non-transitory memory that when executed cause the computing device to: control the x-ray source and the detector array to scan the subject and acquire projection data, reconstruct a first image corresponding to a location of the subject from a subset of the projection data using a first reconstruction technique and reconstruct a second image corresponding to the same location of the subject from the subset of projection data using a second reconstruction technique, different than the first reconstruction technique, calculate an inconsistency metric quantifying temporal inconsistencies between the first image and the second image, responsive to the inconsistency metric not being greater than a threshold, generate a final image of the subset of projection data without applying a motion artifact correction technique, and responsive to the inconsistency metric being greater than the threshold, generate the final image of the subset of projection data with a motion artifact correction technique. In a first example of the system, generating the final image of the subset of projection data without applying a motion artifact correction technique comprises: filtering the first image to remove low frequency content information, filtering the second image to remove high frequency content information, and generating the final image from the filtered first image and the filtered second image. In a second example of the system, optionally including the first example, generating the final image of the subset of projection data with the motion artifact correction technique comprises: filtering the first image to remove low frequency content information, and generating the final image from the filtered first image.

In a third example of the system, optionally including one or both of the first and second examples, the first image is reconstructed with a first reconstruction method and a first view weighting and the second image is reconstructed with the first reconstruction method and a second view weighting, different than the first view weighting. In a fourth example of the system, optionally including one or more or each of the first through third examples, the first reconstruction method comprises an FDK-type reconstruction. In a fifth example of the system, optionally including one or more or each of the first through fourth examples, the first image is reconstructed with a first reconstruction method and the second image is reconstructed with a second reconstruction method, wherein the first reconstruction method and the second reconstruction method comprise one of: an FDK-type reconstruction and a Katsevich-type exact reconstruction, respectively, an FDK-type reconstruction and a Pi-line type exact inversion, respectively, an exact analytic method and an iterative reconstruction, respectively, and an FDK-type reconstruction and an iterative reconstruction, respectively. In a sixth example of the system, optionally including one or more or each of the first through fifth examples, the inconsistency metric quantifies an amount of structures within a difference image between the first image and the second image having mid-range spatial frequencies. In a seventh example of the system, optionally including one or more or each of the first through sixth examples, the inconsistency metric quantifies a total area in a down-sampled difference image between the first image and the second image where an absolute change in pixel brightness is above a threshold value.

The disclosure also provides support for a method for a computed tomography (CT) imaging system, comprising: obtaining projection data of an imaging subject with the CT imaging system, reconstructing a first image from the projection data using a first temporal range of the projection data, reconstructing a second image from the projection data using a second, different temporal range of the projection data, calculating an inconsistency metric quantifying temporal inconsistencies between the first image and the second image, and taking an action based on the inconsistency metric.

When introducing elements of various embodiments of the present disclosure, the articles "a," "an," and "the" are intended to mean that there are one or more of the elements. The terms "first," "second," and the like, do not denote any order, quantity, or importance, but rather are used to distinguish one element from another. The terms "comprising," "including," and "having" are intended to be inclusive and mean that there may be additional elements other than the listed elements. As the terms "connected to," "coupled to," etc. are used herein, one object (e.g., a material, element, structure, member, etc.) can be connected to or coupled to another object regardless of whether the one object is directly connected or coupled to the other object or whether there are one or more intervening objects between the one object and the other object. In addition, it should be understood that references to "one embodiment" or "an embodiment" of the present disclosure are not intended to be interpreted as excluding the existence of additional embodiments that also incorporate the recited features.

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation and use may be made without departing from the principles and concepts set forth herein. Also, as used herein, the examples and embodiments, in all respects, are meant to be illustrative only and should not be construed to be limiting in any manner.

The invention claimed is:

1. A method, comprising:
obtaining projection data of an imaging subject;
reconstructing a first image of a location of the imaging subject from the projection data using a first reconstruction technique and reconstructing a second image corresponding to the same location of the imaging subject from the projection data using a second reconstruction technique, different than the first reconstruction technique in terms of temporal sensitivity;
calculating an inconsistency metric quantifying temporal inconsistencies between the first image and the second image due to motion of the subject, wherein calculating the inconsistency metric comprises calculating the inconsistency metric in image space and spatial frequency space based on the motion, and wherein the inconsistency metric is calculated in image space when the motion is localized to a small area; and
taking an action based on the inconsistency metric, wherein taking an action based on the inconsistency metric comprises applying a motion artifact correction technique to a final image reconstructed from the projection data when the inconsistency metric is greater than a threshold, and not applying a motion artifact correction technique to the final image when the inconsistency metric is not greater than the threshold.

2. The method of claim 1, wherein the first reconstruction technique and the second reconstruction technique comprise different reconstruction methods, and wherein the first reconstruction technique and the second reconstruction technique are from the group selected from Feldkamp-Davis-Kress (FDK)-type reconstructions, Katsevich-type exact reconstruction, Pi-line type exact inversion, exact analytic method, and iterative reconstruction.

3. The method of claim 1, wherein the first reconstruction technique and the second reconstruction technique comprise a same reconstruction method with different view weightings.

4. The method of claim 1, wherein calculating the inconsistency metric comprises generating a difference image representing differences in pixel intensity values between the first image and the second image and calculating the inconsistency metric from the difference image in either a frequency domain or an image domain.

5. The method of claim 4, wherein calculating the inconsistency metric from the difference image in the frequency domain comprises:
applying one or more soft tissue masks to the difference image to generate a masked difference image;
transforming the masked difference image to the frequency domain; and
quantifying an amount of structures with mid-range spatial frequencies, where the inconsistency metric is the amount of structures with the mid-range spatial frequencies.

6. The method of claim 5, wherein calculating the inconsistency metric from the difference image in the image domain comprises:
down-sampling the difference image; and
quantifying a total area in the down-sampled difference image where an absolute change in pixel brightness is above a threshold value, where the inconsistency metric is the total area.

7. The method of claim 6, further comprising band-pass filtering the difference image prior to the down-sampling.

8. The method of claim 1, wherein taking an action based on the inconsistency metric comprises saving the final image and/or displaying the final image.

9. The method of claim 1, wherein taking an action based on the inconsistency metric comprises determining that the inconsistency metric is greater than a second threshold, and in response, outputting a notification of patient motion on a display device.

10. The method of claim 1, wherein obtaining the projection data comprises obtaining the projection data via a computed tomography imaging system, wherein the projection data comprises a subset of projection data of an entire volume of projection data of the imaging subject, and further comprising calculating an additional inconsistency metric for each additional subset of projection data of the entire volume of projection data of the imaging subject and taking an action based on each additional inconsistency metric.

11. An imaging system, comprising:
an x-ray source configured to emit x-rays towards a subject;
a detector array comprising a plurality of detector elements configured to detect x-rays attenuated by the subject;
a computing device communicatively coupled to the x-ray source and the detector array, the computing device configured with instructions in non-transitory memory that when executed cause the computing device to:
control the x-ray source and the detector array to scan the subject and acquire raw projection data;
reconstruct a first image corresponding to a location of the subject from a subset of the raw projection data using a first reconstruction technique and reconstruct a second image corresponding to the same location of the subject from the subset of raw projection data using a second reconstruction technique, different than the first reconstruction technique;
calculate an inconsistency metric quantifying temporal inconsistencies between the first image and the second image due to motion of the subject, wherein calculating the inconsistency metric comprises calculating the inconsistency metric in image space and spatial frequency space based on the motion, and wherein the inconsistency metric is calculated in image space when the motion is localized to a small area;
responsive to the inconsistency metric not being greater than a threshold, generate a final image of the subset of raw projection data without applying a motion artifact correction technique; and
responsive to the inconsistency metric being greater than the threshold, generate the final image of the subset of raw projection data with a motion artifact correction technique.

12. The system of claim 11, wherein generating the final image of the subset of raw projection data without applying a motion artifact correction technique comprises:
filtering the first image to remove low frequency content information;
filtering the second image to remove high frequency content information; and generating the final image from the filtered first image and the filtered second image.

13. The system of claim 12, wherein generating the final image of the subset of raw projection data with the motion artifact correction technique comprises:
    filtering the first image to remove low frequency content information; and
    generating the final image from the filtered first image.

14. The system of claim 11, wherein the first image is reconstructed with a first reconstruction method and a first view weighting and the second image is reconstructed with the first reconstruction method and a second view weighting, different than the first view weighting.

15. The system of claim 14, wherein the first reconstruction method comprises a Feldkamp-Davis-Kress (FDK)-type reconstruction.

16. The system of claim 11, wherein the first image is reconstructed with a first reconstruction method and the second image is reconstructed with a second reconstruction method, wherein the first reconstruction method and the second reconstruction method comprise one of: an FDK-type reconstruction and a Katsevich-type exact reconstruction, respectively; an FDK-type reconstruction and a Pi-line type exact inversion, respectively; an exact analytic method and an iterative reconstruction, respectively; and an FDK-type reconstruction and an iterative reconstruction, respectively.

17. The system of claim 11, wherein the inconsistency metric quantifies an amount of structures within a difference image between the first image and the second image having mid-range spatial frequencies.

18. The system of claim 11, wherein the inconsistency metric quantifies a total area in a down-sampled difference image between the first image and the second image where an absolute change in pixel brightness is above a threshold value.

19. A method for a computed tomography (CT) imaging system, comprising:
    obtaining raw projection data of an imaging subject with the CT imaging system;
    reconstructing a first image from the raw projection data using a first temporal range of the projection data;
    reconstructing a second image from the raw projection data using a second, different temporal range of the projection data;
    calculating an inconsistency metric quantifying temporal inconsistencies between the first image and the second image due to involuntary motion of the imaging subject; and
    taking an action based on the inconsistency metric, wherein the first image has a different magnitude of motion-related artifact than the second image.

* * * * *